(12) United States Patent
Perez et al.

(10) Patent No.: US 7,951,106 B1
(45) Date of Patent: May 31, 2011

(54) PERSONAL HYGIENE DEVICE AND METHOD FOR APPLICATION OF MEDICATION

(75) Inventors: Juan J. Perez, Houston, TX (US);
Stormy L. Perez, Houston, TX (US);
Billie Lane Walker, Spring, TX (US)

(73) Assignee: Juan J. Perez, Houston, TX (US)

( * ) Notice: Subject to any disclaimer, the term of this patent is extended or adjusted under 35 U.S.C. 154(b) by 113 days.

(21) Appl. No.: 12/477,304

(22) Filed: Jun. 3, 2009

(51) Int. Cl.
*A61F 13/20* (2006.01)
(52) U.S. Cl. ............................. 604/11; 604/12; 604/13
(58) Field of Classification Search .............. 604/11–18, 604/378, 385.101, 385.17
See application file for complete search history.

(56) References Cited

U.S. PATENT DOCUMENTS

2003/0225358 A1* 12/2003 Berman et al. .................. 604/11
2008/0300527 A1* 12/2008 Bivins ............................. 604/1

* cited by examiner

*Primary Examiner* — Jacqueline F. Stephens
(74) *Attorney, Agent, or Firm* — Buskop Law Group, PC; Wendy Buskop

(57) ABSTRACT

A personal hygiene device for cleaning orifices, such as the nostrils, one at a time without batteries or power. The device can further be usable in the application of medications, which can be disposed in a tubular body of the device for exact dosage amounts. The personal hygiene device can be reusable without deformation.

19 Claims, 4 Drawing Sheets

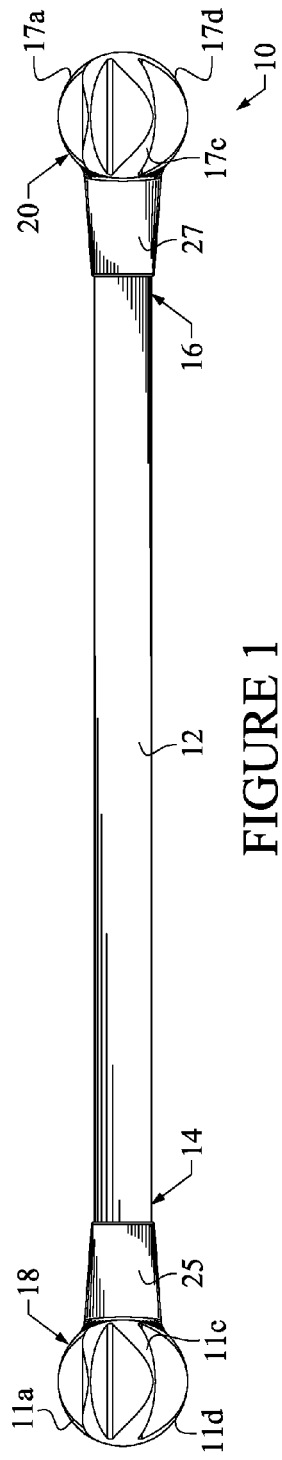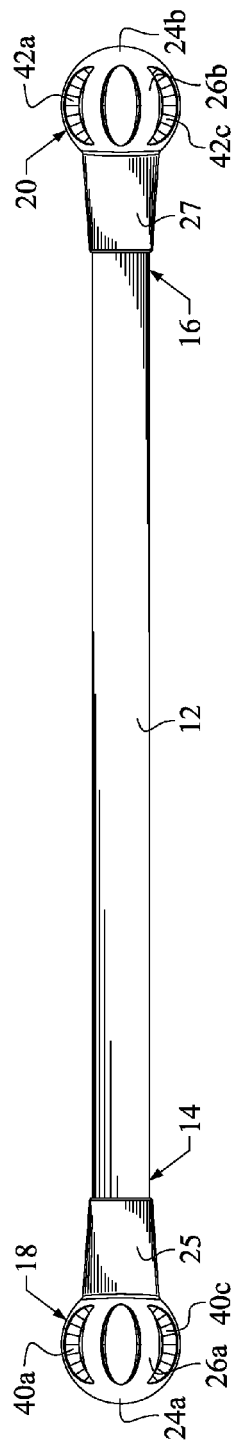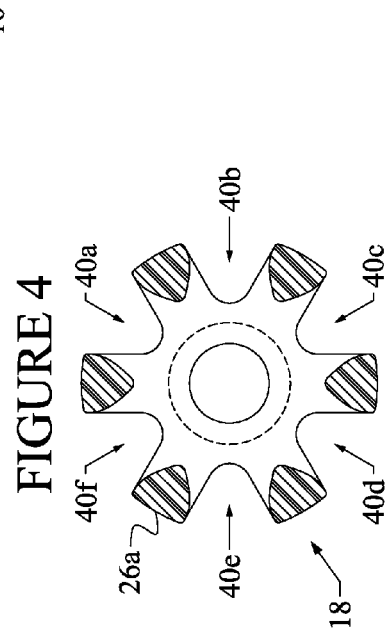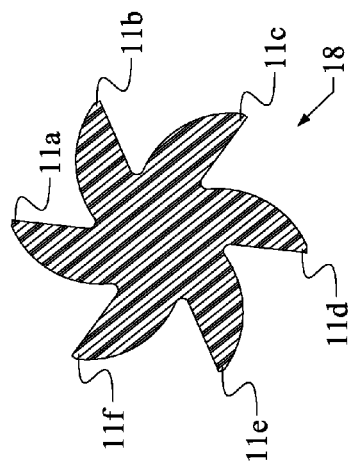

PERSONAL HYGIENE DEVICE AND METHOD FOR APPLICATION OF MEDICATION

FIELD

The present embodiments generally relate to a personal hygiene device for cleaning orifices, such as the nostrils, one at a time without batteries or power. The embodiments further relate to a device for application of a medication, which can be disposed in exact dosage amounts.

BACKGROUND

A need exists for lightweight, simple to use, non-electric powered, personal hygiene device to clean the nostrils of the elderly.

A need exists for a lightweight, simple to use, no-electric powered personal hygiene device that can clean an orifice and additionally act as an applicator of a medication, such as an antibiotic. There has been a need for a simple device that allows precision application of antibiotic creams or for creams that reduce swelling like Cortizone™ in small cavities, like noses of babies.

A further need exists for a lightweight device that can have interchangeable disposable tips which is easy to use by an elderly person or a handicapped person with disabilities.

The present embodiments meet these needs.

BRIEF DESCRIPTION OF THE DRAWINGS

The detailed description will be better understood in conjunction with the accompanying drawings as follows:

FIG. 1 is a side view of the personal hygiene device with solid first and second bulbous ends.

FIG. 2 is a side view of the personal hygiene device with hollow first and second bulbous ends.

FIG. 3 is a cross section of a solid first bulbous end.

FIG. 4 is a cross section of a hollow first bulbous end.

Figure 5:
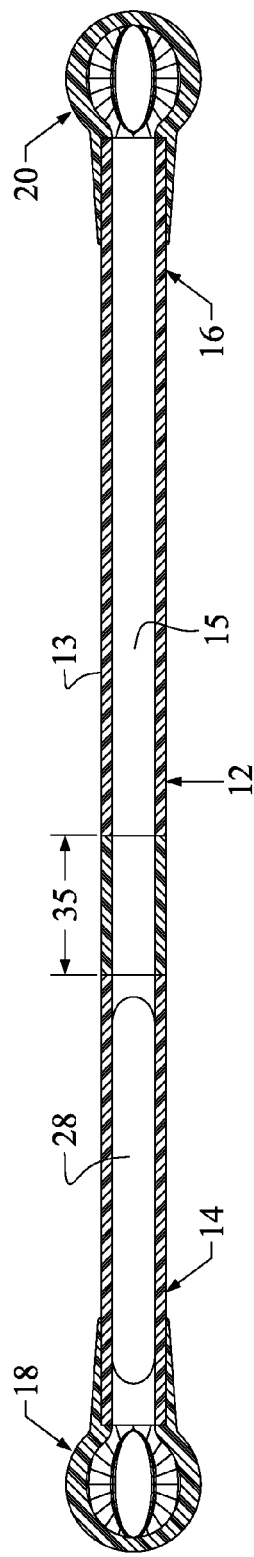
FIG. 5 is a cross sectional view of the personal hygiene device.

The present embodiments are detailed below with reference to the listed Figures.

DETAILED DESCRIPTION OF THE EMBODIMENTS

Before explaining the present apparatus and method in detail, it is to be understood that the apparatus and method is not limited to the particular embodiments, and that it can be practiced or carried out in various ways.

The embodiments relate to an personal hygiene device that can be used for cleaning orifices of a person, such as an elderly person and for the application of medications.

The embodiment relates to a personal hygiene that can be used for both cleaning orifices of a person or an animal, while permitting the precise application of a medication into an orifice, typically a topical application to be applied to the inside of the nostril or the ear.

The embodiments further relate to a one piece unitary device for cleaning nostrils and other orifices that is lightweight and easy to use by a person, such as a handicapped person.

The embodiments can provide the benefit of being flexible, and bendable. The embodiments can further provide the benefit of being a sanitary device that can be cleaned or autoclaved without deforming and reused again, for the embodiment wherein the bulbous ends are solid.

The device can provide pre-measured accurate medication delivery by squeezing the tubular member of the a personal hygiene device while inserting a bulbous end of the device in an orifice, such as the nostril.

The personal hygiene device can be used on humans of all ages, animals, mammals and other living creatures that have at least one nostril or orifice that can be cleaned or medicated using a precise application.

The embodiments can allow the device to be color coded for use of certain pre-filled medications, like all red colored devices can contain a triple antibiotic cream for topical application to the epidermis.

The embodiments can be used to collect specimens from the ears or nose for use in developing a culture, which can provide more tissue than provided using a conventional "cotton swab".

The embodiments can further be useful to scrape tumors or other pre-cancerous tissue that can grow in the tiny areas of the body that are hard to reach, so that analysis of the tissue can be made, without needing to put the patient to sleep or anesthetize the area.

The personal hygiene device can have a tubular body with a first end and a second end. The tubular body can be between about 3 inches to about 8 inches in length.

The tubular body can be solid or hollow, however it must be flexible, bendable and able to bend about 40 degrees from a central axis when the tubular body is in a non-bended form.

The tubular body can be made of a transparent plastic, which can enable the medication and/or creams to be inserted in the hollow body and viewable as "full" or "ready for dosage" from a distance. This "transparent tubular" embodiment can ensure that the medicine is in the tube and ready to be delivered in an exact amount to the precise location or area of the body.

The tubular body can be made of a flexible plastic that can be bent and then return to the non-bent position without permanent deformation.

The tubular body can be contemplated to be made of a non-melting plastic, that is, non-melting in the presence of sunlight or when exposed to temperatures up to about 130 degrees Fahrenheit. This feature can enable the invention to be heat sealed in plastic pouches without deforming for sanitary deployment of the devices.

The tubular body can have a pigment disposed in the plastic or molded polymeric portions. Sparkles can be added to the polymer so that the tubular member medications can be distinguishable, such as blue for a Terramycin™ antibiotic or red sparkles for Cortisone™ disposed in the tubular body.

In an embodiment, the tubular body can be hollow with a capacity for a precise dosage amount of a medication, such as 2 ml. of an antibiotic to be applied to a post cancer treatment portion of a nostril. The medication can be a cream or a gel.

The personal hygiene device can act as a medical device for delivery of medicines to wounded areas that are hard to access, such as a wound in the nostril or an ear.

The device can have a bulbous first end connected to a first tapered sleeve that in turn can secure to the first end of the tubular body. A second tapered sleeve can secure to the second end of the tubular body, and a bulbous second end can be connected to the second tapered sleeve.

The bulbous ends can be integral with the tapered sleeve and tubular body or the bulbous ends can be threadably connected to the tubular body.

In another embodiment the bulbous ends can be force fit onto the tubular body.

In still another embodiment the bulbous ends can be fastened to the tubular body with an adhesive or an epoxy or a similar strong fastening chemical.

The bulbous ends can each have a diameter between about 1/8 inch to about 1/2 inch in cross section, regardless of whether they are hollow or solid. The flexible tubular body can have a diameter in cross section no more than about 1/2 the diameter of the bulbous first and second ends. For an embodiment to be used by an adult, the bulbous ends can use a diameter of about 3/8 inch. For an embodiment to be used by a child, the bulbous ends can use a diameter of about 1/4 inch.

For the solid version of the bulbous ends, the ends can use a first and second projecting edge that in an embodiment taper to an apex. For this embodiment, an adult size embodiment can contemplate using between about 6 projecting edges to about 8 projecting edges. For a child size embodiment about 4 projecting edges can be used.

In an embodiment, the personal hygiene device can have a plurality of first and a second projecting edges, wherein each edge can have a flat face. The flat face can further have a textured surface.

The solid bulbous ends can be made from Polyetheretherketone (PEEK). Other polymers can be used such as polypropylene or polyethylene or another crystalline polymer that resist deformation upon minor pressure.

For another solid version of the bulbous ends, the ends can use a first and second projecting edge that can taper to a face. The face can have a texture on it, such as about 10 mini-bumps to about 20 mini-bumps.

For the hollow version of the bulbous ends, each end can be made up of a slightly stiff but flexible plastic forming a generally spherical hollow body. Crystalline homopolymers and copolymers of propylene and ethylene such an ethylene-propylene copolymer can be usable, as well as molded PEEK, with very thin walls.

The generally spherical hollow body can have a wall thickness of between about 0.020 inch to about 0.060 inch.

The generally spherical hollow body can be injection molded. The bulbous ends can be injected molded separately, enabling different sized bulbous ends to be used with the tubular body, or injection molded with the tubular body forming a one piece unit.

The bulbous ends can each have a solid top which can be smooth which can further prevent damage to tissue for insertion. For the hollow body embodiment, the bulbous ends can have sides with a plurality of perforations which can be of various shapes, such as elongated shapes or round shapes, and sizes.

An embodiment can contemplate that the perforations can be equidistantly spaced around the spherical hollow body.

Another embodiment can contemplate that the perforations can be grouped on one side of the spherical hollow body.

At least about 3 perforations to about 8 perforations per bulbous ends can be contemplated as usable herein.

An embodiment can contemplate that a medication can be inserted in the tubular body or in at least one of the hollow bulbous ends.

The medication can be a member of the group consisting of: an antibiotic, a Cortisone™, an antiallergen, such as Benedryl™ cream, an antihistamine, such as Caladryl™ or combinations of these types of medications.

It can be contemplated that the tubular body can be preloaded with the medication for dispensing into the bulbous first and second ends by squeezing the hollow tube at a center portion which is referred to herein as a compression zone. The tubular body can have at least one or more compression zones, depending on how much medication needs to be dispensed and from which end of the tubular body dispensing needs to occur.

It can be contemplated that the tubular body can be designed and sized to be held between a users' thumb and forefinger.

An embodiment can contemplate that a cover, which can be clear thermoplastic rigid cover or hermetically sealed pouch, can be disposed over at least one bulbous end, both ends, or the entire device to keep the ends or the device clean for further usage.

An embodiment can contemplate that the plurality of perforations can be a plurality of slots between about 4.3656 millimeters to about 5.5563 millimeters in length and about 1.6 millimeters to about 2.3813 millimeters in width.

Another embodiment can contemplates that the side of the bulbous ends can have a textured surface formed in the surface to enable easier cleaning of the skin, nostril. ear or tongue.

The personal hygiene device can further be used to clean nostrils, ears, navels, or small body openings or portions of the mouth.

Turning now to the Figures, FIG. 1 is a side view of an embodiment of the personal hygiene device 10 with a first bulbous end 18 and a second bulbous end 20. The first bulbous end 18 can be attached to a first tapered sleeve 25, which can in turn be attached to a first end 14 of a flexible tubular body 12. The second bulbous end 20 can be attached to a second tapered sleeve 27 which can in turn be attached to a second end 16 of the flexible tubular body 12.

It can also be contemplated that the personal hygiene device 10 can be an integral one piece molded polymeric device.

It can also be contemplated that the diameter of each first and second bulbous end can be between about 1/8 inch to about 1/2 inches. The flexible tubular body 12 can have a diameter no more than about 1/2 the diameter of the bulbous first and second bulbous ends.

Figure 6:
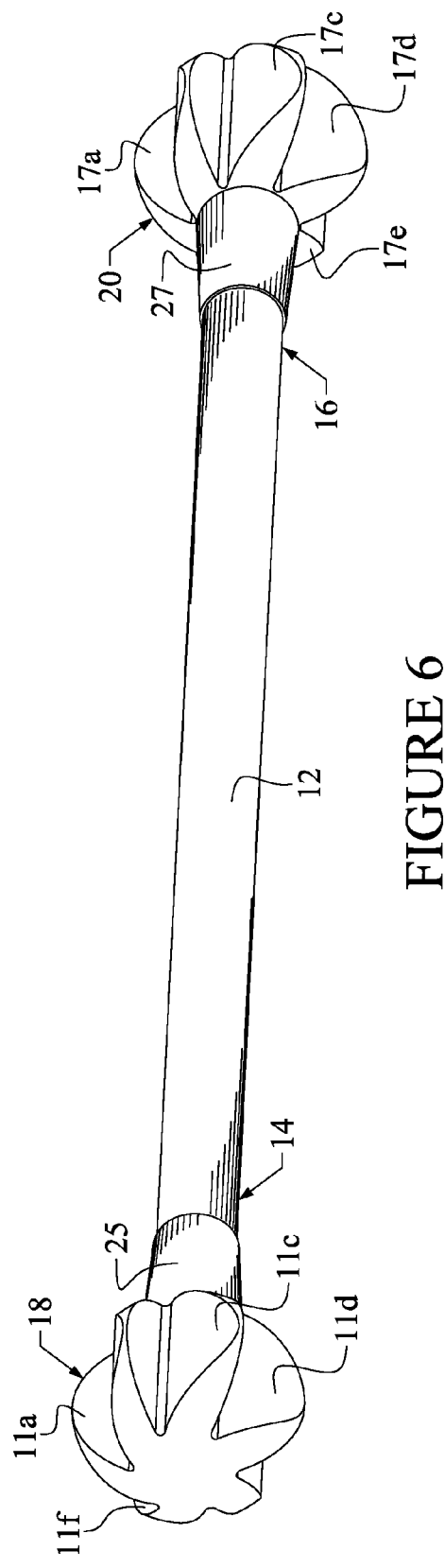
FIG. 6 is a perspective view of an embodiment of the invention wherein the first bulbous end and second bulbous end are solid.

The first bulbous end can be solid and comprise a plurality of first projecting edges 11a-11f, shown in more detail in FIG. 6 The second bulbous end can also be solid an comprise a plurality of second projecting edges 17a-17f, shown in more detail in FIG. 3 and FIG. 6.

It can be contemplated that the plurality of first and second projecting edges can be a rounded shape, a rectangular shape, or any other geometric shape.

It can also be contemplated that the first and second bulbous ends can be hollow, as seen in FIG. 2.

FIG. 2 shows a side view of the personal hygiene device 10 with the first bulbous end 18 and the second bulbous end 20. The first bulbous end 18 can be a generally spherical hollow body that can have a solid top 24a and a first side 26a with a plurality of first perforations 40a-40f. The second bulbous end 20 can also be a generally spherical hollow body that can have a solid top 24b and a second side 26b with a plurality of second perforations 42a-42f.

It can be contemplated that the first and second plurality of perforations can be a plurality of slots between about 0.3 millimeters to about 0.5 millimeters in length and about 0.1 millimeters to about 0.2 millimeters in width with an elongated shape.

The first bulbous end 18 can be attached to a first tapered sleeve 25, which can in turn be attached to a first end 14 of the hollow flexible tubular body 12. The second bulbous 20 end can be attached to a second tapered sleeve 27 which can in turn be attached to a second end 16 of the flexible tubular body 12.

FIG. 3 is a cross sectional of the first bulbous end 18 in which the first bulbous end is solid. Each of the first projecting edges 11*a*-11*f* is shown in this Figure.

While FIG. 3 shows six first projecting edges, as many as eight and as few as 3 projecting edges can be used.

FIG. 4 is a cross sectional of the first bulbous end 18 in which the first bulbous end is hollow. Each of the plurality of first perforations 40*a*-40*f* in the first side 26*a* is shown in this Figure.

While FIG. 4 shows six first perforations, as many as eight and as few as three perforations can be used.

FIG. 5 is a cross sectional view of the personal hygiene device 10 with the flexible tubular body 12. FIG. 5 shows the flexible tubular body 12 has a flexible tubular body outer wall 13 and a flexible tubular body inner wall 15. Within the inner wall 15 can be a medication 28, such as a cream or gel. The medication can be a member of the group consisting of: an antibiotic, a Cortisone™, an antiallergen, an antihistamine, or combinations thereof.

In an embodiment it can be contemplated that the flexible tubular body can be made of a transparent flexible polymer. It can also be contemplated that a pigment, sparkles, or printed indicators, can be used to indicate the type of medication in the flexible tubular body.

A first compression zone 35 is shown wherein a user can compress the flexible tubular body in this zone between the thumb and forefinger and cause dispensing of the medication into at least one of the first bulbous end 18, the second bulbous end 20, or both simultaneously into the ear or other part of the body needing treatment FIG. 6 shows a perspective view of an embodiment, wherein the first bulbous end 18 and second bulbous end 20 are solid polymer. Shown in this Figure is the flexible tubular body 12 with a first bulbous end 18 and a second bulbous end 20. On the first and second bulbous ends are the first projecting edges 11*a*-11*f* and the second projecting edges 17*a*-17*f* Also shown is the first tapered sleeve 25 and the second tapered sleeve 27.

Figure 7:
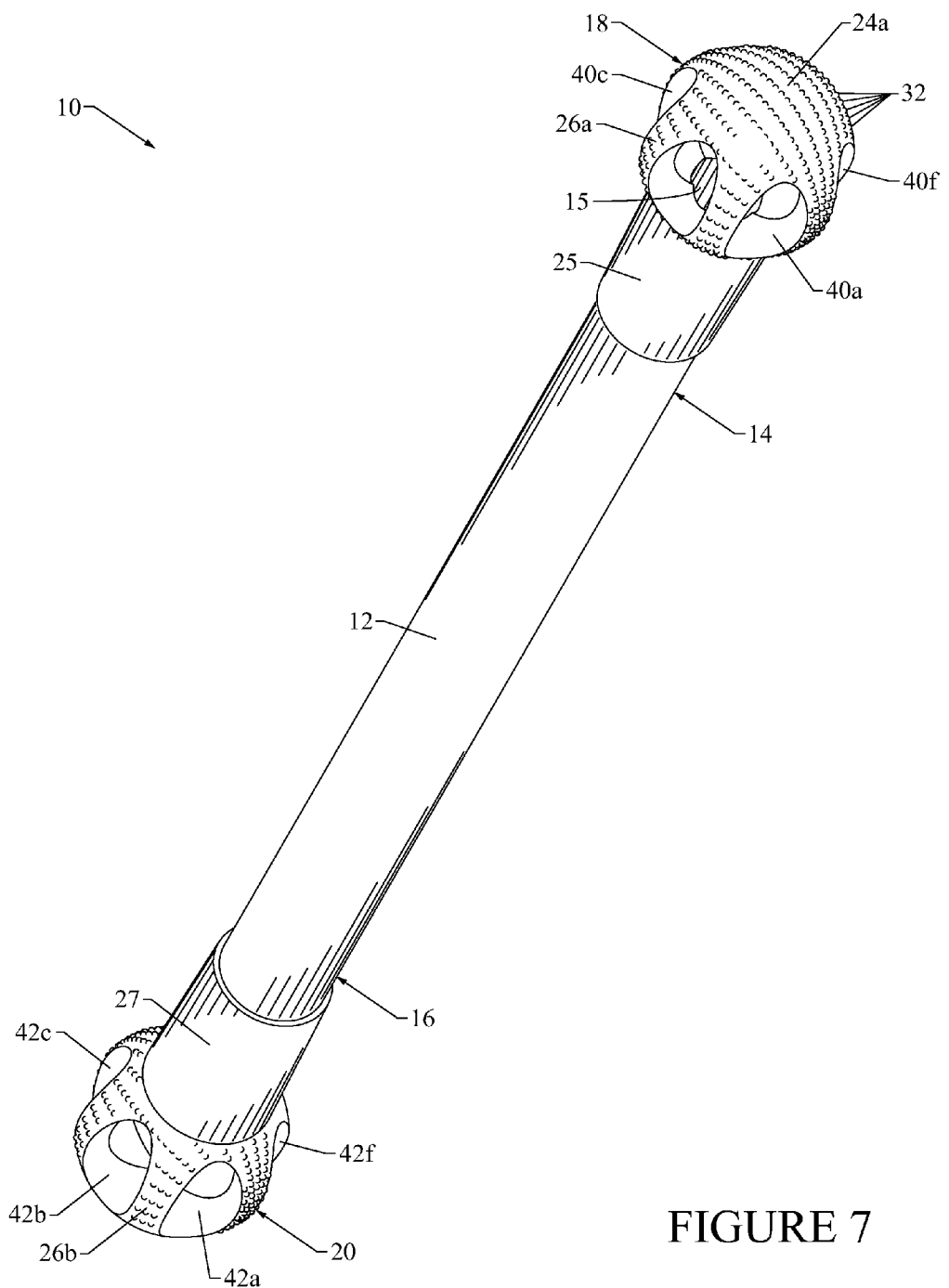
FIG. 7 is a perspective view of an embodiment of the invention wherein the first bulbous end and second bulbous end are hollow with a textured surface.

FIG. 7 shows a perspective view of the personal hygiene device 10. The flexible tubular body 12 with a hollow first bulbous end 18 and a hollow second bulbous end 20 is shown.

The first bulbous end 18, with a plurality of first perforations 40*a*-40*f* in the first side wall 26*a*, is shown secured to the flexible tubular body 12 with a first tapered sleeve 25. The solid top 24*a* of the first bulbous end 18 is also visible in this Figure.

Also shown if FIG. 7 is the second bulbous end 20, with a plurality of second perforations 42*a*-42*f* in the second side wall 26*b*, shown secured to the flexible tubular body 12 with a second tapered sleeve 27.

FIG. 7 also shows a the first and second bulbous ends with a textured surface 32. It can be contemplated that the textured surface can cover the first and second side walls 26*a*, 26*b* of the first and second bulbous ends, the first and second solid tops 24*a*, 24*b*, or combinations thereof.

The textured surface can consist of a plurality of protruding bumps of any geometric shape, a plurality of indentions of any geometric shape, or combinations thereof.

Figure 8:
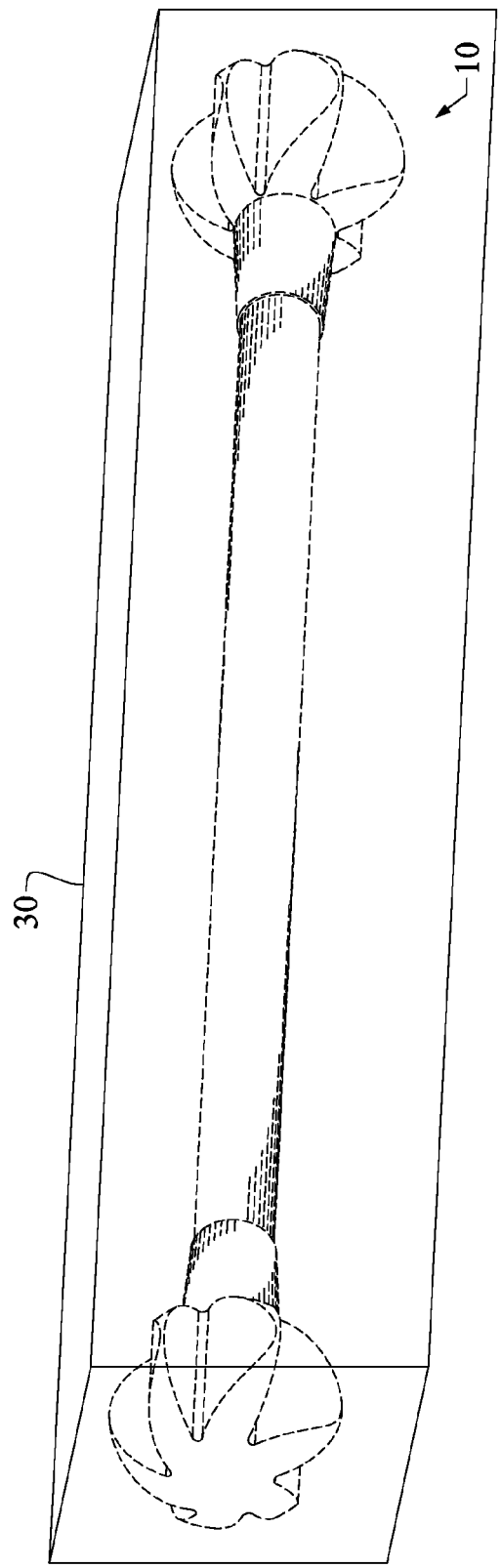
FIG. 8 is a perspective view of the personal hygiene device inside a removable cover.

FIG. 8 shows a perspective view of the personal hygiene device 10 inside a removable cover 30.

The removable cover 30 can encapsulates the personal hygiene device 10 or be disposed over at least one of the bulbous ends. The removable cover 30 can form a hermetic seal and prevent the personal hygiene device 10 or the medication therein from becoming contaminated. The removable cover 30 can also aid in the prevention of tampering with the personal hygiene device 10 or the medication therein.

While these embodiments have been described with emphasis on the embodiments, it should be understood that within the scope of the appended claims, the embodiments might be practiced other than as specifically described herein.

What is claimed is:

1. A personal hygiene device comprising:
   a. a flexible tubular body with a first end and a second end, wherein the flexible tubular body comprises a flexible tubular body inner wall and a flexible tubular body outer wall, and wherein a medication is disposed within the flexible tubular body inner wall;
   b. a first tapered sleeve connected to the first end;
   c. a second tapered sleeve connected to the second end;
   d. a first bulbous end connected to the first tapered sleeve wherein the first bulbous end comprises a plurality of first projecting edges; and
   e. a second bulbous end connected to the second tapered sleeve, wherein the second bulbous end comprises a plurality of second projecting edges and wherein the second bulbous end, the first bulbous end, or both are configured to dispense the medication when the flexible tubular body is compressed in a compression zone.

2. The personal hygiene device of claim 1, wherein the first and second projecting edges are rounded.

3. The personal hygiene device of claim 1, wherein the tubular body, the first and second tapered sleeves, the first bulbous end and the second bulbous end are an integral one piece molded polymeric device.

4. The personal hygiene device of claim 1 wherein the diameter of the first bulbous end and the second bulbous second end is between ⅛ inch to ½ inch in cross section and wherein the flexible tubular body has a diameter in cross section no more than ½ the diameter of the first and second bulbous ends.

5. The personal hygiene device of claim 1, wherein the first and second projecting edges each have a flat face.

6. The personal hygiene device of claim 5, wherein each flat fate has a textured surface.

7. The personal hygiene device of claim 1, wherein the device is an orifice cleaning device.

8. A personal hygiene device comprising:
   a. a flexible tubular body with a first end and a second end, wherein the flexible tubular body comprises a flexible tubular body inner wall and a flexible tubular body outer wall, and wherein a medication is disposed within the flexible tubular body inner wall;
   b. a first tapered sleeve connected to the first end;
   c. a second tapered sleeve connected to the second end;
   d. a first bulbous end connected to the first tapered sleeve, wherein the first bulbous end is a generally spherical hollow body having a solid top and a side with a plurality of perforations; and
   e. a second bulbous end connected to the second tapered sleeve, wherein the second bulbous end is a generally spherical hollow body having a solid top and a side, and a plurality of perforations; and wherein the second bulbous end, the first bulbous end, or both are configured to dispense the medication when the flexible tubular body is compressed in a compression zone.

9. The personal hygiene device of claim 8 wherein the flexible tubular body is a transparent flexible polymer.

10. The personal hygiene device of claim 8, wherein the diameter of the first bulbous end and the second bulbous end is between ⅛ inch to ½ inch in cross section and wherein the flexible tubular body has a diameter in cross section no more than ½ the diameter of the first and second bulbous ends.

11. The personal hygiene device of claim 8, wherein at least one of the generally spherical hollow bodies contains a medication.

12. The personal hygiene device of claim 11, wherein the medication is a member of the group consisting of: an antibiotic, a Cortisone™, an antiallergen, an antihistamine, or combinations thereof.

13. The personal hygiene device of claim 8, further comprising a removable cover disposed over at least one of the bulbous ends.

14. The personal hygiene device of claim 13, wherein the removable cover encapsulates the personal hygiene device.

15. The personal hygiene device of claim 8, wherein the plurality of perforations are a plurality of slots between 4 millimeters to 6 millimeters in length and 1 millimeter to 2.5 millimeters in width with an elongated shape.

16. The personal hygiene device of claim 8, wherein the side has a textured surface.

17. The personal hygiene device of claim 8, wherein the device is an orifice cleaning device.

18. The personal hygiene device of claim 8, wherein the plurality of perforations range between 3 slots to 8 slots per bulbous end.

19. The personal hygiene device of claim 8, wherein the tubular body comprises: a pigment, sparkles, or printed indicators, to indicate the type of medication in the tubular body.

* * * * *